(12) United States Patent
Platt, Jr. et al.

(10) Patent No.: US 6,458,321 B1
(45) Date of Patent: Oct. 1, 2002

(54) STERILIZATION SYSTEM EMPLOYING LOW FREQUENCY PLASMA

(75) Inventors: Robert C. Platt, Jr., Laguna Niguel; Mitch Agamohamadi, Orange, both of CA (US)

(73) Assignee: Ethicon, Inc., New Brunswick, NJ (US)

( * ) Notice: Subject to any disclaimer, the term of this patent is extended or adjusted under 35 U.S.C. 154(b) by 0 days.

(21) Appl. No.: 09/676,919

(22) Filed: Oct. 2, 2000

(51) Int. Cl.[7] .............................. A61L 2/00; A61L 9/00
(52) U.S. Cl. ............................ 422/23; 422/22; 422/28; 422/292; 422/295; 422/299
(58) Field of Search ............................ 422/22, 23, 26, 422/27, 28, 292, 295, 299

(56) References Cited

U.S. PATENT DOCUMENTS

| | | | |
|---|---|---|---|
| 3,876,373 A | | 4/1975 | Glyptis .......................... 422/22 |
| 4,643,876 A | | 2/1987 | Jacobs et al. .................. 422/22 |
| 4,756,882 A | * | 7/1988 | Jacobs et al. .................. 422/23 |
| 5,087,418 A | * | 2/1992 | Jacob .......................... 422/23 |
| 5,302,343 A | | 4/1994 | Jacob .......................... 422/23 |
| 5,448,155 A | * | 9/1995 | Jutras .......................... 323/285 |
| 5,512,244 A | | 4/1996 | Griffiths et al. ............... 422/23 |
| 5,528,109 A | * | 6/1996 | Ilcisin et al. ............. 315/169.4 |
| 5,656,238 A | | 8/1997 | Spencer et al. ............... 422/23 |
| 5,737,204 A | * | 4/1998 | Brown .......................... 363/89 |
| 5,747,972 A | * | 5/1998 | Baretich et al. ............. 323/223 |
| 5,876,663 A | * | 3/1999 | Laroussi ...................... 422/23 |
| 6,060,019 A | | 5/2000 | Spencer et al. ............... 422/23 |

* cited by examiner

Primary Examiner—Robert J. Warden, Sr.
Assistant Examiner—Imad Soubra
(74) Attorney, Agent, or Firm—Knobbe, Martens, Olson & Bear, LLP (57) ABSTRACT

A method and system for sterilizing an article is provided that includes use of a low frequency (LF) gas discharge plasma. The method includes placing the article in a vacuum chamber and evacuating the vacuum chamber to a predetermined pressure. Gas or vapor species are introduced into the vacuum chamber, and a low frequency plasma is generated within the vacuum chamber, the low frequency plasma having a frequency of from 0 to approximately 200 kHz. The low frequency plasma is maintained for a time period sufficient to substantially remove gas or vapor species from the article. The sterilization system includes a vacuum chamber coupled to a vacuum pump and a vent, a first electrode, and a second electrode. The sterilization system further includes a first region within the vacuum chamber, the first region including a region between the first and second electrodes, and a second region within the vacuum chamber, the second region being in fluid communication with the first region. The sterilization system further includes a source of reactive agent species coupled to the vacuum chamber, a process control monitor, and a low frequency power module including components adapted to apply a low frequency voltage between the first electrode and second electrode to generate a low frequency plasma in the vacuum chamber, the low frequency voltage having a frequency of from 0 to approximately 200 kHz.

33 Claims, 10 Drawing Sheets

STERILIZATION SYSTEM EMPLOYING LOW FREQUENCY PLASMA

BACKGROUND OF THE INVENTION

1. Field of the Invention

The invention relates to systems and methods for sterilizing articles that include the use of a gas discharge plasma.

2. Description of the Related Art

Plasmas produced using radio frequency (RF) generators in particular have proven to be valuable tools in processes for the sterilization of medical devices. For example, in U.S. Pat. Nos. 4,643,876 and 4,756,882, which are incorporated by reference herein, Jacobs, et al. disclose using hydrogen peroxide as a precursor in a low temperature sterilization system that employs RF plasma. The combination of hydrogen peroxide vapor and a RF plasma provides an efficient method of sterilizing medical devices without, using or leaving highly toxic materials or forming toxic by-products. Similarly, Jacob, U.S. Pat. No. 5,302,343, and Griffiths, et al., U.S. Pat. No. 5,512,244, teach the use of RF plasmas in a sterilization process.

However, there are problems associated with the use of an RF plasma in a sterilization process. The RF plasma may leave residual hydrogen peroxide on the sterilized article. The residual amount of hydrogen peroxide remaining on the sterilized article depends upon the RF power applied to the article, the amount of time exposed to the RF plasma, and the material of the article. For example, while some plastics (e.g., polyurethane) absorb hydrogen peroxide, other materials (e.g., Teflon) absorb relatively little, thereby yielding less residual hydrogen peroxide after sterilization.

In addition, inherent inefficiencies in the energy conversion from the low frequency (e.g., 60 Hz) line voltage to the RF (e.g., approximately 1 MHz–1 GHz) voltage used to generate the RF plasma limit the power efficiency of such systems to typically less than 50%. Energy efficiency is further reduced by typically 5–20% by virtue of the losses from the required impedance matching network between the RF generator and the load. Such low energy efficiency significantly increases the cost per watt applied to the sterilized articles. The required instrumentation for using RF electrical energy (e.g., RF generator, impedance matching network, monitoring circuitry) is expensive, which also increases the cost per watt applied to the sterilized articles.

SUMMARY OF THE INVENTION

One aspect of the present invention is a method of sterilization of an article. The method comprises placing the article in a vacuum chamber and evacuating the vacuum chamber to a predetermined pressure. Gas or vapor species are introduced into the vacuum chamber, and a low frequency plasma is generated within the vacuum chamber, the low frequency plasma having a frequency of from 0 to approximately 200 kHz. The low frequency plasma is maintained for a time period sufficient to substantially remove gas or vapor species from the article.

Another aspect of the present invention is a method of sterilization of an article. The method comprises placing the article in a vacuum chamber and evacuating the vacuum chamber to a predetermined pressure. A low frequency plasma is generated within the vacuum chamber, the low frequency plasma having a frequency of from 0 to approximately 200 kHz. The low frequency plasma is maintained for a time period sufficient to heat the article to aid the evaporation and removal of water and other absorbed gases from the vacuum chamber and the article.

Another aspect of the present invention is a system for sterilizing an article. This system comprises a vacuum chamber coupled to a vacuum pump and a vent, a first electrode, and a second electrode. The system further comprises a first region within the vacuum chamber, the first region comprising a region between the first and second electrodes. The system further comprises a second region within the vacuum chamber, the second region being in fluid communication with the first region. The system further comprises a source of fluid coupled to the vacuum chamber, a process control monitor, and a low frequency power module comprising components adapted to apply a low frequency voltage between the first electrode and second electrode to generate a low frequency plasma in the vacuum chamber, the low frequency voltage having a frequency of from 0 to approximately 200 kHz.

BRIEF DESCRIPTION OF THE DRAWINGS

FIG. 3, which is broken into FIGS. 3a and 3b, schematically illustrates an embodiment of a low frequency power module compatible with the phase angle control method of the present invention.

FIG. 4, which is broken into FIGS. 4a and 4b, schematically illustrates an embodiment of a low frequency power module compatible with the amplitude control method of the present invention.

DETAILED DESCRIPTION OF THE PREFERRED EMBODIMENT

Production of gas discharge plasmas using low frequency (LF) voltages avoids the various problems inherent in the state of the art sterilization devices and processes which form and use plasmas produced by radio frequency (RF) voltages. First, LF plasma processing leaves less residual reactive species remaining on the sterilized articles than does RF plasma processing. Second, generation of the LF plasma is highly energy efficient because little or no frequency conversion from the line voltage is needed. For example, by using no frequency conversion with a line voltage frequency of 60 Hz, the energy efficiency of the sterilization system can reach approximately 85–95%. Use of LF voltages also does not require an impedance matching network, thereby avoiding the associated energy losses. Third, due to the simplified instrumentation and higher energy efficiency of LF generation, the cost per watt applied to the sterilized articles using LF plasmas can be as low as one-tenth the cost per watt of using RF plasmas. Fourth, the simplified instrumentation used for generating LF plasmas has proven to be more reliable and robust, and requiring less complicated diagnostic instrumentation.

Figure 1:
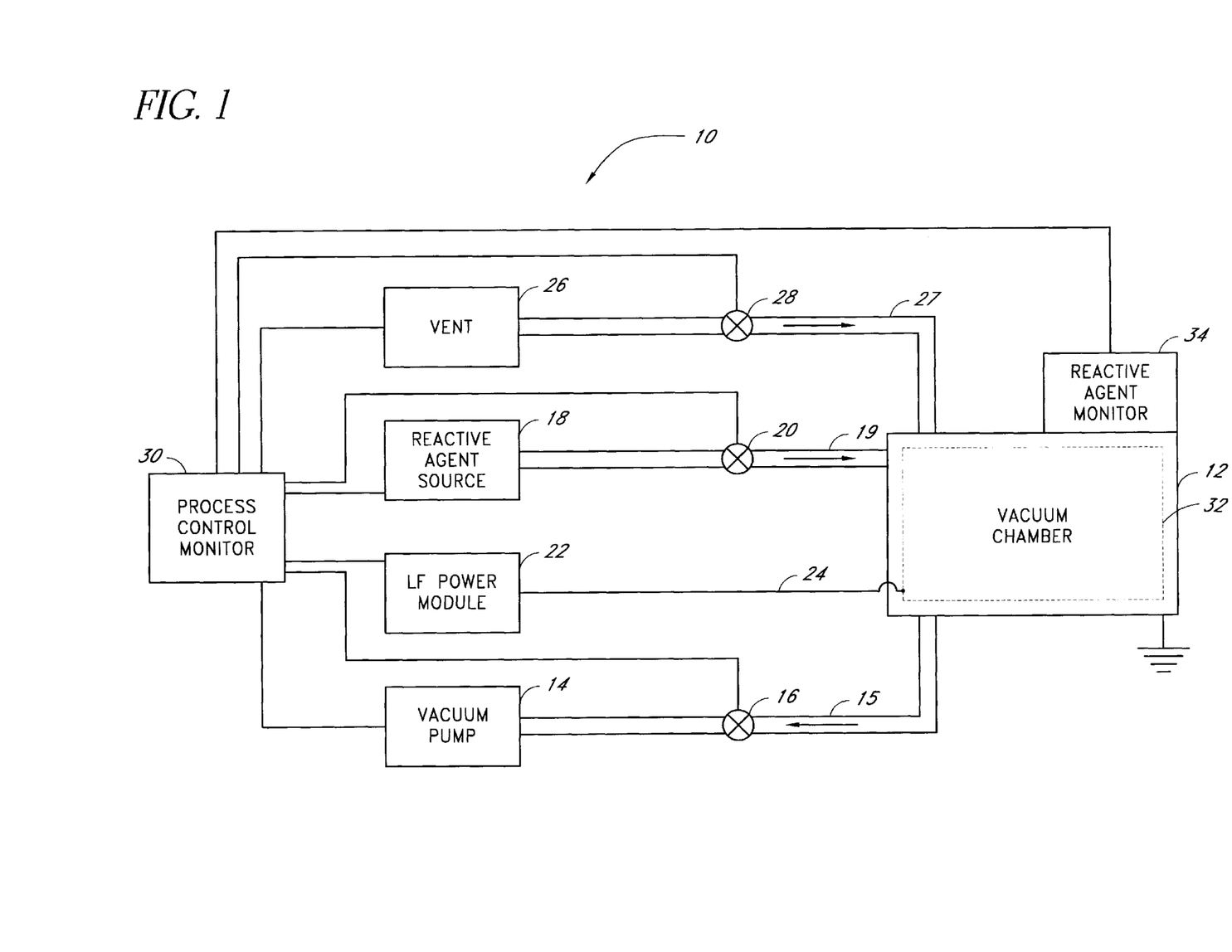
FIG. 1 schematically illustrates a preferred embodiment of a sterilization system compatible with the present invention.

FIG. 1 schematically illustrates one preferred embodiment of the present invention comprising a sterilization system 10. The sterilization system 10 comprises a vacuum chamber 12, a vacuum pump 14, a vacuum pump line 15, a vacuum pump valve 16, a reactive agent source 18, a reactive agent line 19, a reactive agent valve 20, a low frequency (LF) power module 22, an LF voltage conduit 24, a vent 26, a vent line 27, a vent valve 28, a process control module 30, an electrode 32, and a reactive agent monitor 34. Persons skilled in the art recognize that other embodiments comprising sterilization systems of different configurations than that illustrated in FIG. 1 are compatible with the present invention.

In the preferred embodiment of the present invention, the articles (not shown in FIG. 1) to be sterilized are packaged in various commonly employed packaging materials used for sterilized products. The preferred materials are spun-bonded polyethylene packaging material commonly available under the trademark "TYVEK" or composites of "TYVEK" with a polyethylene terephthalate packaging material commonly available under the trademark "MYLAR". Other similar packaging materials may also be employed such as polypropylene. Paper packaging materials may also be used. With paper packaging, longer processing times may be required to achieve sterilization because of possible interactions of the reactive agent with paper.

The vacuum chamber 12 of the preferred embodiment is sufficiently gas-tight to support a vacuum of approximately less than 40 Pa (0.3 Torr). Coupled to the vacuum chamber 12 is a pressure monitor (not shown) which is also coupled to the process control module to provide a measure of the total pressure within the vacuum chamber. Also coupled to the vacuum chamber 12 is the reactive agent monitor 34 which is capable of detecting the amount of the reactive agent in the vacuum chamber 12. In the exemplary embodiment of the present invention, the reactive agent is hydrogen peroxide, and the reactive agent monitor 34 measures the absorption of ultraviolet radiation at a wavelength characteristic of hydrogen peroxide. Other methods of reactive agent detection compatible with the present invention include, but are not limited to, pressure measurement, near infrared absorption, and dew point measurement. The reactive agent monitor 34 is also coupled to the process control module 30 to communicate the detected amount of the reactive agent to the process control module 30.

In the preferred embodiment of the present invention, inside and electrically isolated from the vacuum chamber 12 is the electrode 32, which is electrically conductive and perforated to enhance fluid communication between the gas and plasma species on each side of the electrode 32. The electrode 32 of the preferred embodiment generally conforms to the inner surface of the vacuum chamber 12, spaced approximately one to two inches from the wall of the vacuum chamber 12, thereby defining a gap region between the vacuum chamber 12 and the electrode 32. The electrode 32 is coupled to the LF power module 22 via the LF voltage conduit 24. In the preferred embodiment, with the vacuum chamber 12 connected to electrical ground via a bypass capacitor and shunt resistor, application of an LF voltage between the vacuum chamber 12 and the electrode 32 creates an LF electric field which is stronger in a first region 31 which includes the gap region and the vicinity of the edges of the electrode 32. The LF electric field is weaker in a second region 33 where the sterilized articles are placed. Generally, in other embodiments, the LF electric field can be generated by applying an LF voltage between the electrode 32 and a second electrode in the vacuum chamber 12. In such embodiments, the first region 31 includes the gap region between the two electrodes, and the vicinity of the edges of one or both of the electrodes. The preferred embodiment in which the vacuum chamber 12 serves as the second electrode is one of the many different ways to generate the gas plasma.

Figure 2A:
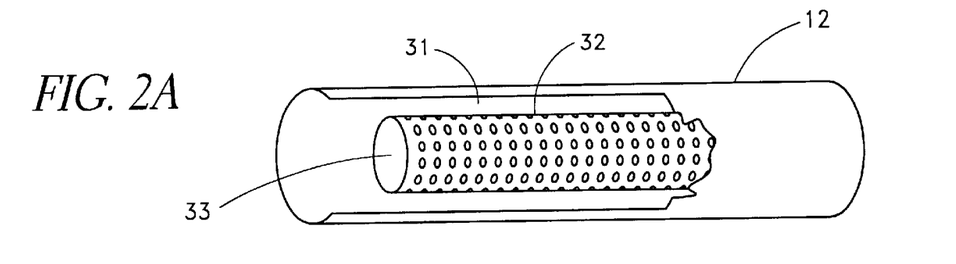
FIG. 2A schematically illustrates a preferred embodiment of a cylindrically-shaped electrode with open ends and perforated sides.
Figure 2B:
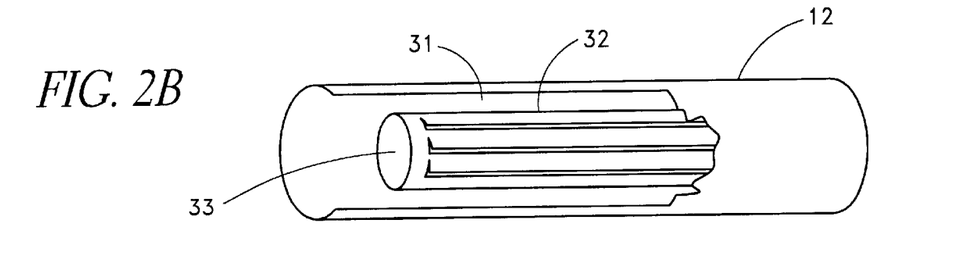
FIG. 2B schematically illustrates an alternative embodiment of a cylindrically-shaped electrode with open ends and louvered sides.
Figure 2C:
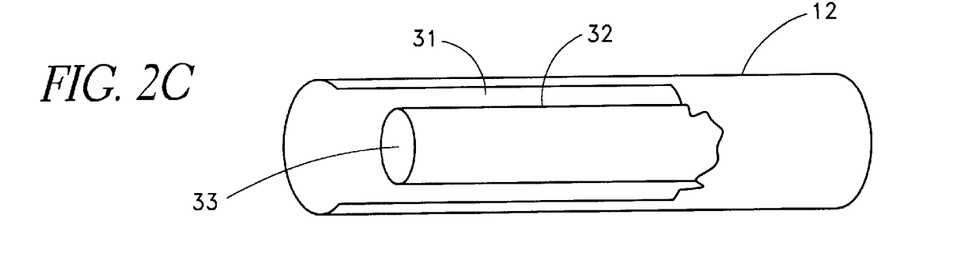
FIG. 2C schematically illustrates an alternative embodiment of a cylindrically-shaped electrode with open ends and solid sides.
Figure 2D:
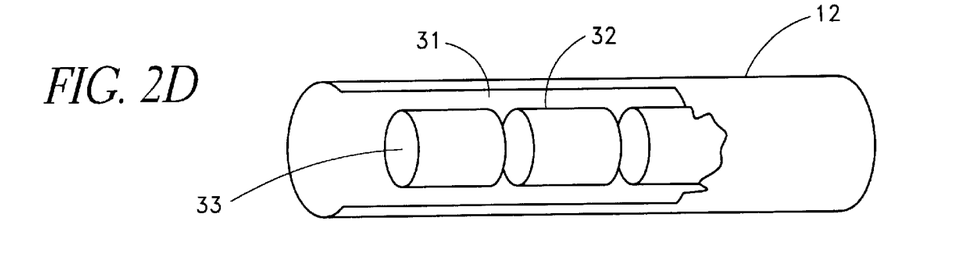
FIG. 2D schematically illustrates an alternative embodiment of an electrode comprising one or more colinear cylindrically-shaped segments with open ends and solid sides.
Figure 2E:
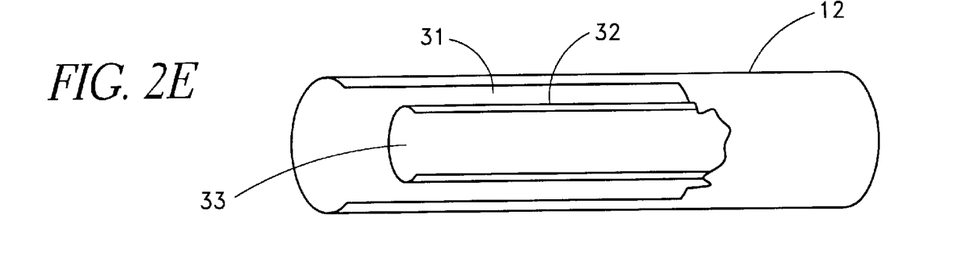
FIG. 2E schematically illustrates an alternative embodiment of an electrode with a partial cylindrical shape, open ends, and solid sides.
Figure 2F:
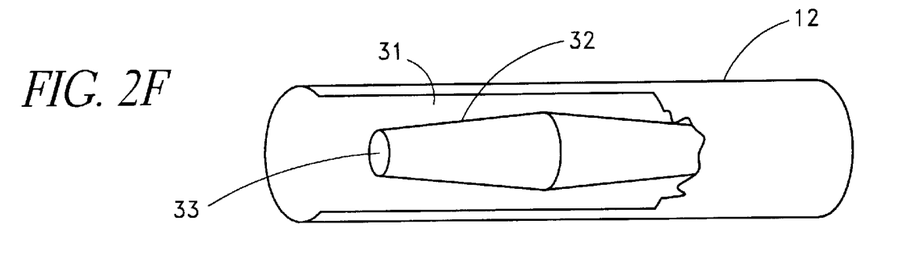
FIG. 2F schematically illustrates an alternative embodiment of a cylindrically-symmetric and longitudinally-asymmetric electrode with open ends and solid sides.
Figure 2G:
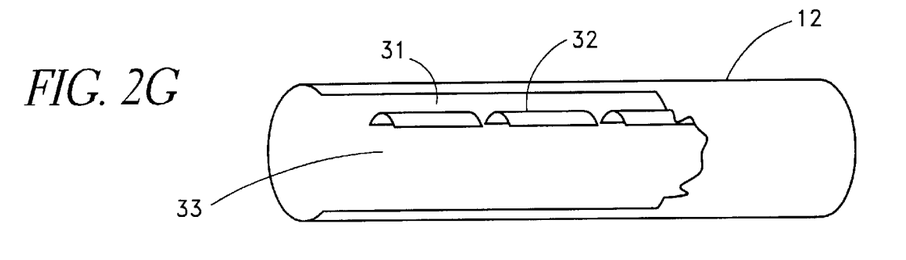
FIG. 2G schematically illustrates an alternative embodiment of one or more asymmetric electrodes with open ends and solid sides.
Figure 2H:
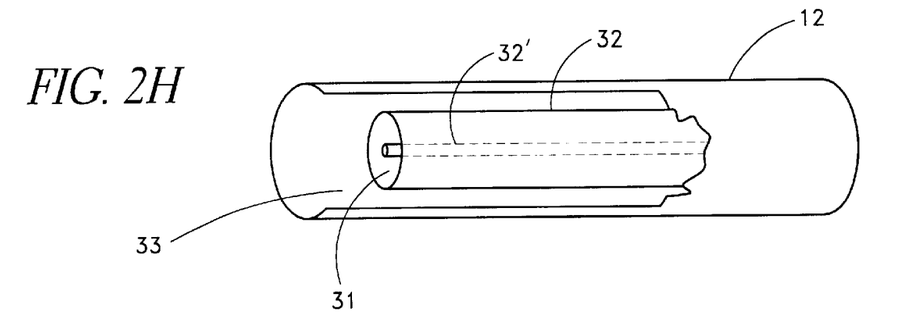
FIG. 2H schematically illustrates an alternative embodiment of an electrode system with a first electrode that is cylindrically-shaped with open ends and solid sides, and a second electrode comprising a wire substantially colinear with the first electrode.
Figure 2I:
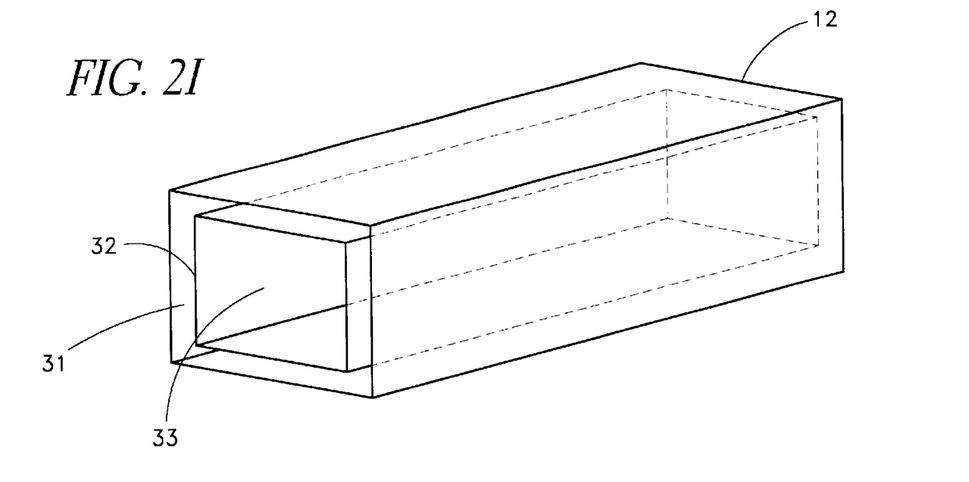
FIG. 2I schematically illustrates an alternative embodiment of a generally square or rectangular electrode within a generally square or rectangular vacuum chamber.

In the preferred embodiment illustrated in FIG. 2A, a cylindrically-shaped electrode 32 provides fluid communication between the gas and plasma on each side of the electrode 32 through the open ends of the electrode 32 as well as through the perforations in the side of the electrode 32. These open ends and perforations permit gaseous and plasma species to freely travel between the first region 31 between the electrode 32 and the walls of the vacuum chamber 12 and the second region 33 where the sterilized articles are placed. Similarly, as illustrated in FIGS. 2B–2I, other configurations of the electrode 32 provide fluid communication between the first region 31 and the second region 33. FIG. 2B schematically illustrates a cylindrically-shaped electrode 32 with open ends and, louvered openings along its sides. FIG. 2C schematically illustrates a cylindrically-shaped electrode 32 with open ends and solid sides. FIG. 2D schematically illustrates an electrode 32 comprising a series of colinear cylindrically-shaped segments with open ends and solid sides. FIG. 2E schematically illustrates an electrode 32 with a partial cylindrical shape, open ends and solid sides. FIG. 2F schematically illustrates a cylindrically-symmetric and longitudinally-asymmetric electrode 32 with open ends and solid sides. FIG. 2G schematically illustrates an asymmetric electrode 32 with open ends and solid sides. More than one electrode can be used to generate the plasma. FIG. 2H schematically illustrates an electrode system with a first electrode 32 that is cylindrically-shaped with open ends and solid sides, and a second electrode 32' comprising a wire substantially colinear with the first electrode 32. The LF voltage is applied between the first electrode 32 and the second electrode 32'. In this embodiment, the first region 31 is the region between the first electrode 32 and the second electrode 32', and the second region 33 is between the first electrode 32 and the vacuum chamber 12. FIG. 2I schematically illustrates a generally square or rectangular electrode within a generally square or rectangular vacuum chamber. The various configurations for generally cylindrical electrodes schematically illustrated in FIGS. 2A–2H can also be applied to the generally square or rectangular electrode of FIG. 2I. Each of these embodiments of the electrode 32 provide fluid communication between the first region 31 and the second region 33.

The vacuum pump 14 of the preferred embodiment is coupled to the vacuum chamber 12 via the vacuum pump line 15 and the vacuum valve 16. Both the vacuum pump 14 and the vacuum pump valve 16 are coupled to, and controlled by, the process control module 30. By opening the vacuum valve 16, gases within the vacuum chamber 12 are pumped out of the vacuum chamber 12 through the vacuum pump line 15 by the vacuum pump 14. In certain embodiments, the vacuum valve 16 is capable of being opened to variable degrees to adjust and control the pressure in the vacuum chamber 12.

The reactive agent source 18 of the preferred embodiment is a source of fluid coupled to the vacuum chamber 12 via the reactive agent line 19 and the reactive agent valve 20. The reactive agent valve 20 is coupled to, and controlled by, the process control module 30. The reactive agent source 18 of the preferred embodiment comprises reactive agent species. In the preferred embodiment, the reactive agent species comprises a germicide which is a sterilant or a disinfectant, such as hydrogen peroxide. In addition, the germicide supplied by the reactive agent source 18 can be in gas or vapor form. By opening the reactive agent valve 20, reactive agent atoms and molecules from the reactive agent, source 18 can be transported into the vacuum chamber 12 via the reactive agent line 19. In certain embodiments, the reactive agent valve 20 is capable of being opened to variable degrees to adjust the pressure of the reactive agent in the vacuum chamber 12. In the exemplary embodiment of the present invention, the reactive agent species of the reactive agent source 18 comprising hydrogen peroxide molecules.

The vent 26 of the preferred embodiment is coupled to the vacuum chamber 12 via the vent line 27 and the vent valve 28. The vent valve 28 is coupled to, and controlled by, the process control module 30. By opening the vent valve 28, vent gas is vented into the vacuum chamber 12 via the vent line 27. In certain embodiments, the vent valve 28 is capable of being opened to variable degrees to adjust the pressure of the air in the vacuum chamber 12. In the exemplary embodiment of the present invention, the vent 26 is a High Efficiency Particulate-filtered, Air (HEPA) vent which provides filtered air as the vent gas. Other vent gases compatible with the present invention include, but are not limited to, dry nitrogen, and argon.

The process control module 30 is coupled to various components of the sterilization system 10 to control the sterilization system 10. In an exemplary embodiment of the present invention, the process control module 30 is a microprocessor configured to provide control signals to the various other components in response to the various signals received from other components.

Figures 3, 3A:
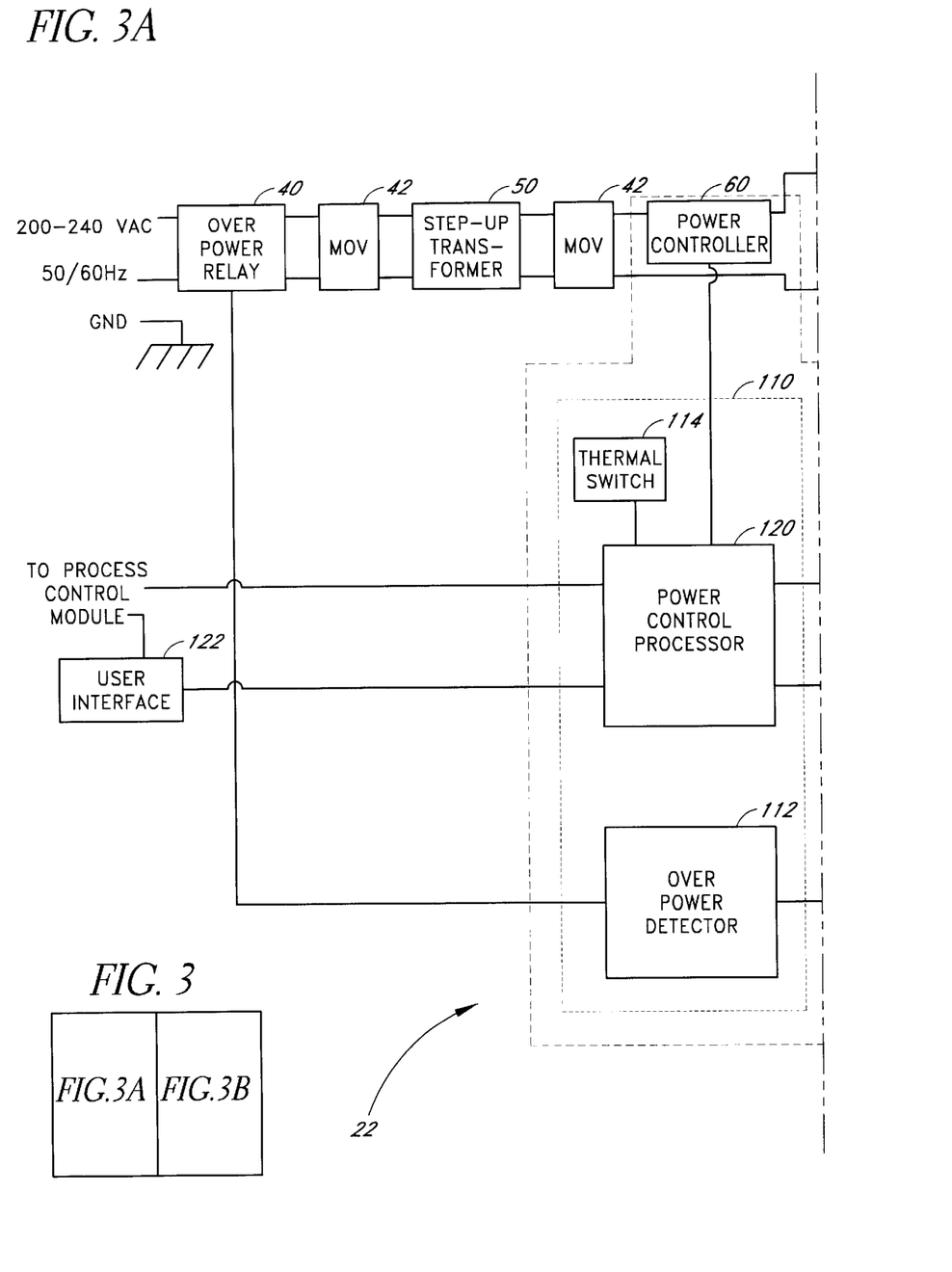
Figure 3B:
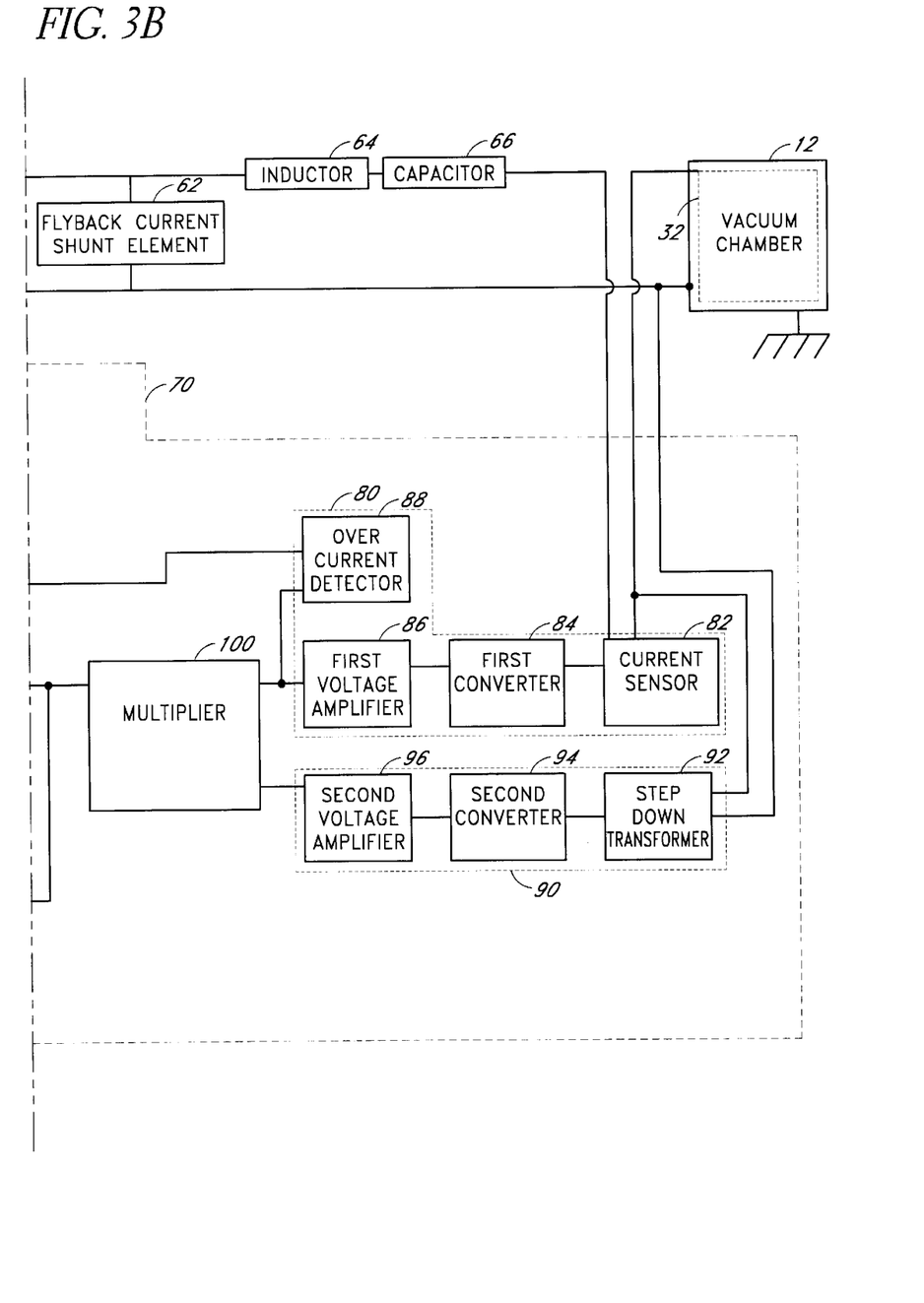

The LF power module 22 of the preferred embodiment is coupled to the electrode 32 via the LF voltage conduit 24, and is coupled to, and controlled by, the process control module 30. The LF power module 22 is adapted to apply a low frequency voltage between the electrode 32 and the vacuum chamber 12 so as to generate a low frequency plasma in the vacuum chamber 12. FIG. 3, which is broken into FIGS. 3a and 3b, schematically illustrates an embodiment of the LF power module 22 compatible with the phase angle control method of controlling the low frequency power applied to the plasma. As illustrated in FIG. 3, the LF power module 22 comprises an over-power relay 40, a pair of metal oxide varistors 42, a step-up transformer 50, a flyback current shunt element 62, an inductor 64, a capacitor 66, and a LF power feedback control system, 70. The LF power feedback control system 70 illustrated in FIG. 3 comprises a power controller 60, a current monitor 80, a voltage monitor 90, and a power monitor 100 coupled to the current monitor 80 and the voltage monitor 90. Line voltage (typically 200–240 VAC, 50/60 Hz) is provided to the step-up transformer 50 via the closed over-power relay 40 which is coupled to the LF power feedback control system 70. For other frequencies, the LF power module 22 may also include a switching module to provide lower frequencies or frequencies up to a few hundred kHz.

In the embodiment illustrated in FIG. 3, the metal oxide varistors (MOVs) 42 are used to suppress transient voltage impulses. Each MOV 42 is a multiple-junction solid-state device capable of withstanding large magnitude impulses with a low amount of let-through voltage. The MOVs 42 serve as fast acting "variable resistors" with a low impedance at higher-than-normal voltages and a high impedance at normal voltages. MOVs are manufactured for specific voltage configurations and for a variety of impulse magnitudes. Persons skilled in the art are able to select MOVs 42 consistent with the present invention.

The output voltage of the step-up transformer 50 is preferably between approximately 100 and 1000 $V_{rms}$, more preferably between approximately 200 and 500 $V_{rms}$, and most preferably between approximately 250 and 450 $V_{rms}$. The output voltage of the step-up transformer 50 is transmitted to the power controller 60, which provides the LF voltage to the electrode 32 and vacuum chamber 12 via the flyback current shunt element 62, the inductor 64, the capacitor 66, and the LF power feedback control system 70. The flyback current shunt element 62 provides a path for fly-back current and to tune the circuit, and in the preferred embodiment the flyback current shunt element 62 is a load resistor of approximately 1500 ohms. In other embodiments, the flyback current shunt element 62 can be a snubber. The inductance of the inductor 64 is chosen to limit noise spikes in the LF current, and is typically approximately 500 mH. The capacitance of the capacitor 66 is chosen to maximize the efficiency of power transfer to the LF plasma by matching the resonant frequency of the series LC circuit to the frequency of the applied LF voltage. For a 60 Hz voltage and an inductance of 500 mH, a capacitance of approximately 13.6 $\mu F$ provides the resonant condition for which the impedance of the series LC circuit is approximately zero, thereby maximizing the transmitted LF power. Persons skilled in the art are able to select appropriate values for these components depending on the frequency of the applied LF voltage in a manner compatible with the present invention.

Figures 4, 4A:
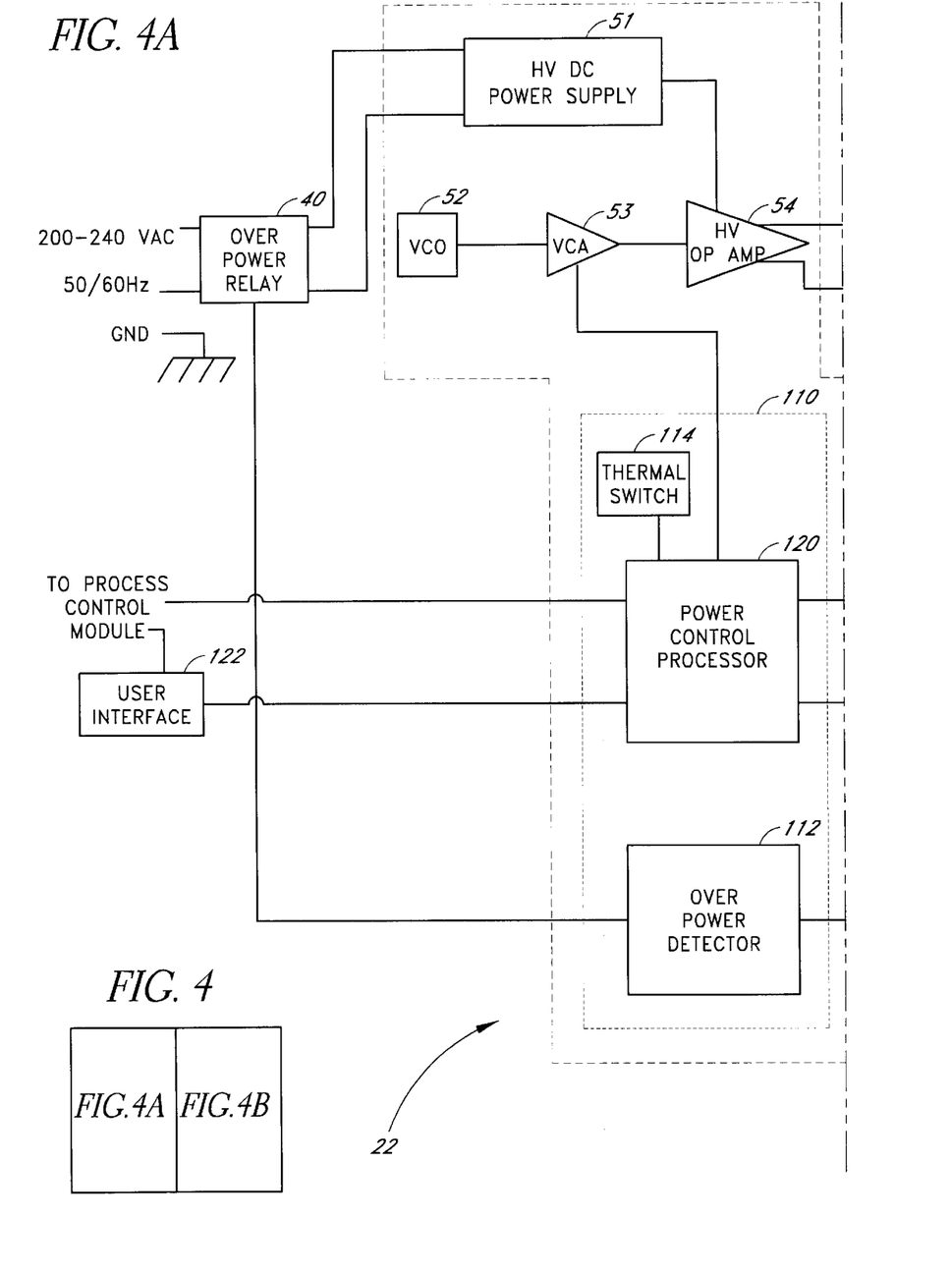
Figure 4B:
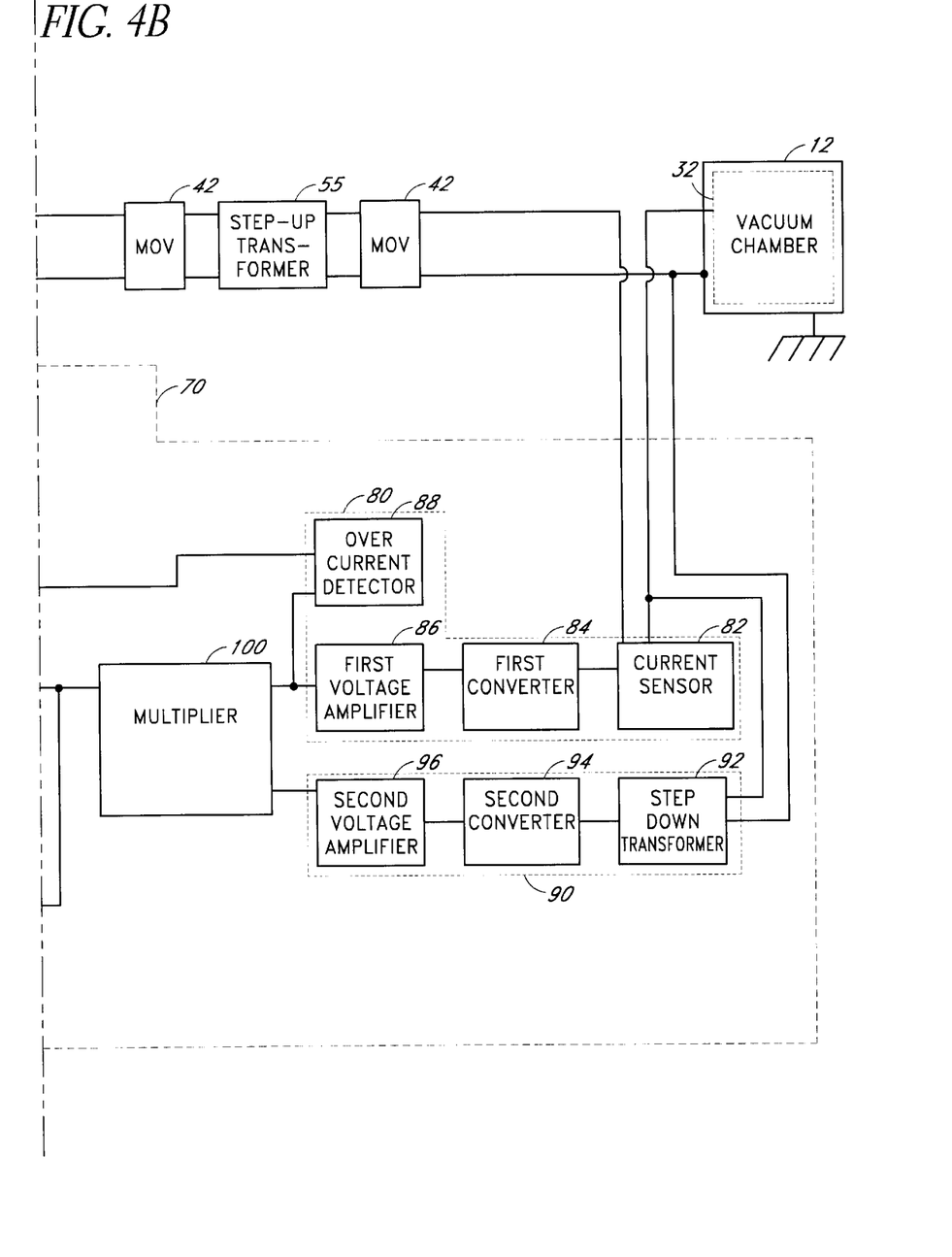

FIG. 4, which is broken into FIGS. 4a and 4b, schematically illustrates an embodiment of the LF power module 22 compatible with the amplitude control method of controlling the low frequency power applied to the plasma. As illustrated in FIG. 4, the LF power module 22 comprises an over-power relay 40, a pair of metal oxide varistors 42, a step-up transformer 55, and a LF power feedback control system 70. The LF power feedback control system 70 illustrated in FIG. 4 comprises a high voltage (HV) DC power supply 51, a voltage-controlled oscillator (VCO) 52, a voltage-controlled amplifier (VCA) 53, a HV operational amplifier 54, a current monitor 80, a voltage monitor 90, and a power monitor 100 coupled to the current monitor 80 and the voltage monitor 90. Line voltage is provided to the HV DC power supply 51 via the closed over-power relay 40 which is coupled to the LF power feedback control system 70. The output of the HV DC power supply 51 is preferably between approximately 100 and 1000 VDC, more preferably between approximately 200 and 500 VDC, and most preferably between approximately 250 and 450 VDC.

In the embodiment illustrated in FIG. 4, the VCO 52 generates a sinewave output with a constant amplitude and fixed low frequency from 0 to 1 MHz, the low frequency selected by supplying an appropriate set-point voltage to the VCO 52. Alternative embodiments can utilize other waveforms, e.g., triangular or square waveforms. The LF output of the VCO 52 is supplied to the VCA 53, which serves as a power controller to maintain a substantially stable average power applied to the low frequency plasma. In response to a feedback signal from the power control module 110, the VCA 53 amplifies the LF output of the VCO 52 to generate an amplified LF voltage with an amplitude between approximately 0 and 12 VAC. The amplified LF voltage from the VCA 53 is supplied to the HV operational amplifier 54 which in response generates a high voltage LF output with an amplitude determined by the amplitude of the amplified LF voltage from the VCA 53. Appropriate HV operational amplifiers are commercially available (e.g., Apex Microtechnology, Tuscon, Ariz., part number PA93), and persons skilled in the art are able to select a HV operational amplifier compatible with the present invention. Typically, the amplitude of the high voltage LF output from the HV operational amplifier 54 is approximately 100 to 150 VAC. In order to generate larger amplitude LF voltages to be applied to the plasma, the high voltage LF output from the HV operational amplifier 54 can be further amplified by the step-up transformer 55, as illustrated in FIG. 4. Alternatively, the step-up transformer 55 may be omitted if the HV operational amplifier 54 is capable of generating a high voltage LF output with the desired amplitude to be applied to the plasma.

In both the phase angle control embodiment illustrated in FIG. 3 and the amplitude control embodiment illustrated in FIG. 4, the LF power feedback control system 70 of the LF power module 22 further comprises a power control module 110 coupled to the power monitor 100, which is coupled to the current monitor 80 and voltage monitor 90. The current monitor 80 measures the LF current through the electrode 32 and the vacuum chamber 12. In the preferred embodiment of the present invention, the current monitor 80 includes a current sensor 82 which provides a voltage output indicative of the measured real-time, cycle-by-cycle LF current, a first converter 84 which produces a DC voltage in response to the RMS of the voltage output of the current sensor 82, and a first voltage amplifier 86 which amplifies the DC voltage from the first converter 84 to produce a real-time current signal. In addition, the current monitor 80 also includes an over-current detector 88, which monitors the DC voltage from the first converter 84 in real-time and sends an error signal to the power control module 110 if the LF current exceeds a pre-set value, caused for example by a short circuit between the electrode 32 and the vacuum chamber 12. Under such an occurrence, the LF voltage is turned off momentarily. This occurrence can result in a few cycles being lost, however the power is stabilized so that the average power is not affected by more than a predetermined tolerance.

The voltage monitor 90 measures the LF voltage between the electrode 32 and the vacuum chamber 12. In the preferred embodiment of the present invention, the voltage monitor 90 includes a step-down transformer 92 which produces a voltage output indicative of the measured real-time, cycle-by-cycle LF voltage, a second converter 94 which produces a DC voltage in response to the RMS of the voltage output of the step-down transformer 92, and a second voltage amplifier 96 which amplifies the DC voltage from the second converter 94 to produce a real-time voltage signal.

In the preferred embodiment, the power monitor 100 further comprises a multiplier that receives the DC voltages from the current monitor 80 and the voltage monitor 90, and multiplies these two voltages to produce a real-time power signal proportional to the LF power applied to the plasma between the electrode 32 and the vacuum chamber 12, the real-time power signal being generated in response to the real-time current and real-time voltage signals, and transmitted to the power control module 110. In other embodiments, the power monitor 100 monitors the power applied to the plasma by utilizing a signal indicative of the real-time impedance of the plasma with either the real-time current or real-time voltage signals. In still other embodiments, the power monitor 100 monitors the power applied to the plasma by utilizing other real-time signals which indirectly indicate the power applied to the plasma; e.g., a real-time signal proportional to the brightness of the glow discharge generated by the plasma. Persons skilled in the art can select an appropriate power monitor 100 compatible with the present invention.

The power control module 110 of the preferred embodiment includes a fault detector, such as an over-power detector 112 which monitors the real-time power signal from the power monitor 100 and opens the over-power relay 40 if the LF power exceeds a pre-set value, thereby extinguishing the LF plasma. After such an occurrence, the control of restart can be given to the user or to software. The power control module 110 of the preferred embodiment further comprises an additional fault detector, such as a thermal switch 114 which detects overheating, and a power control processor 120.

In the preferred embodiment; the power control processor 120 controls and monitors the status of the LF power feedback control system 70. The power control processor 120 is coupled to a user interface 122 which provides user input regarding a selected power magnitude setting and a selected power on/off setting. The power control processor 120 is also coupled to the power monitor 100, the thermal switch 114, and the over-current detector 88. In the preferred embodiment, the power magnitude setting can be selected from two power levels, 800 W and 600 W. When the power is turned on, the preferred embodiment of the power control processor 120 ensures that a "soft start" condition is maintained in which the inrush current is minimized. In addition, the user interface 122 receives signals from the power control processor 120 indicative of the status of the sterilization system 10, which is communicated to the user.

In the phase angle control embodiment illustrated in FIG. 3, the power control processor 120 is also coupled to the power controller 60. In this embodiment, the power control processor 120 transmits a signal to the power controller 60 in response to signals from the user interface 122, power monitor 100, over-current detector 88, and thermal switch 114 in order to maintain a substantially stable LF power applied to the LF plasma while avoiding error conditions. In the amplitude control embodiment illustrated in FIG. 4, the power control processor 120 is coupled to the VCA 53. In this embodiment, the power control processor 120 transmits a signal to the VCA 53 in response to signals from the user interface 122, power monitor 100, over-current detector 88, and thermal switch 114 in order to maintain a substantially stable LF power applied to the LF plasma while avoiding error conditions. In both embodiments illustrated in FIG. 3 and FIG. 4, the power control processor 120 typically maintains the LF power applied to the LF plasma within a tolerance of approximately 0–10% of the specified power level.

Note that not all of the components listed and described in FIG. 3 and FIG. 4 are required to practice the present invention, since FIG. 3 and FIG. 4 merely illustrate particular embodiments of the LF power module 22. These components include components for automation, safety, regulatory, efficiency, and convenience purposes. Other embodiments compatible with the present invention can eliminate some or all of these components, or can include additional components.

Figure 5A:
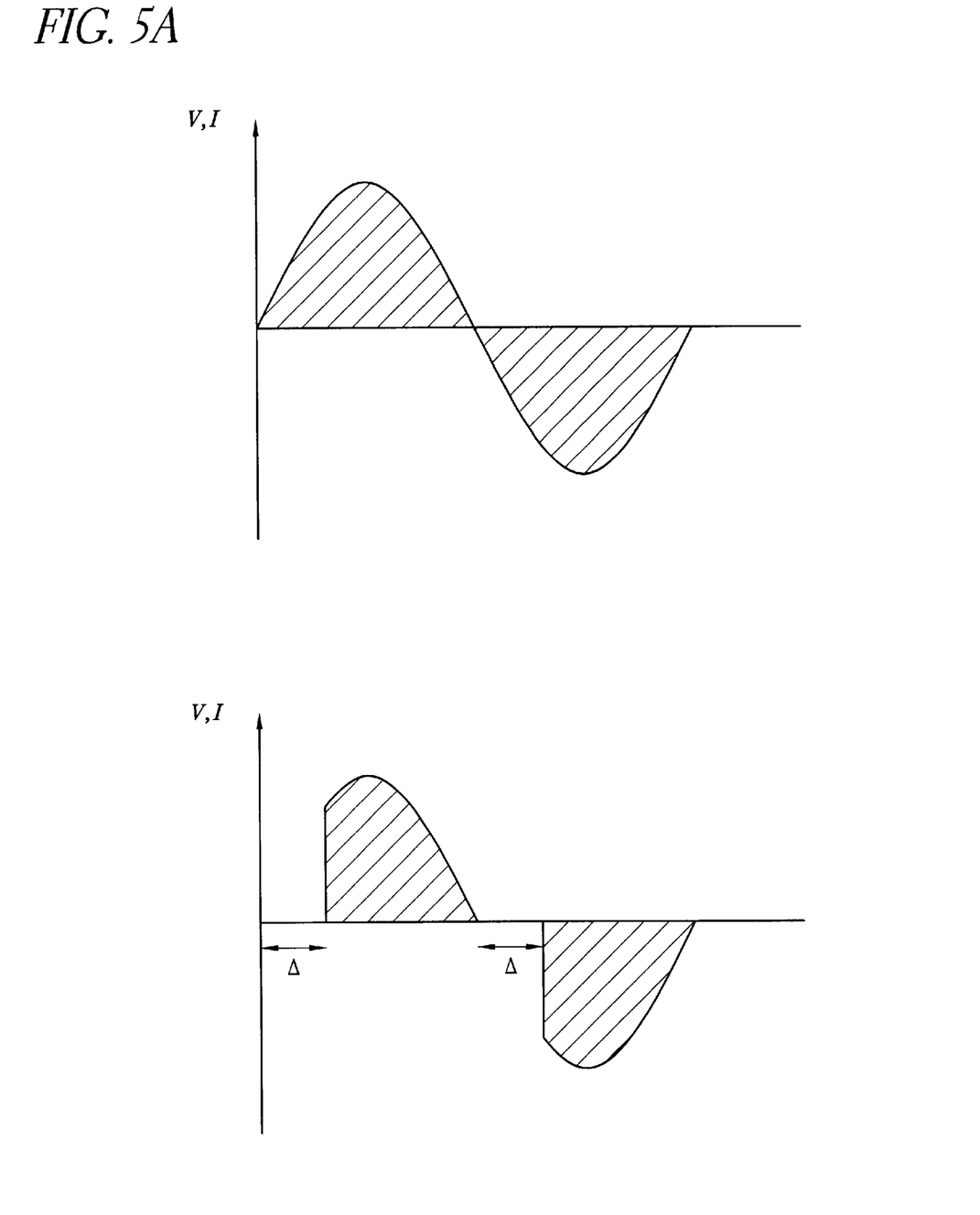
FIG. 5A schematically illustrates the phase angle control method of controlling the low frequency power applied to the plasma.

In response to the signal from the power control processor 120, the power controller 60 of the embodiment illustrated in FIG. 3 controls the LF power applied between the electrode 32 and the vacuum chamber 12 by utilizing phase angle control. Under phase angle control, the duty cycle of the LF power is modified by zeroing the voltage and current applied between the electrode 32 and the vacuum chamber 12 for a portion Δ of the cycle period. Such phase angle control is often used to maintain constant power from electric heaters or furnaces. FIG. 5A schematically illustrates the voltage and current for a 100% duty cycle (i.e., Δ=0) and for a reduced duty cycle (i.e., Δ≠0). During normal operations, the power controller 60 maintains a constant LF power applied to the plasma by actively adjusting the duty cycle of the LF power in response to the feedback real-time signal received from the power control module 110 in response to the measured LF power. When a fault event is detected by the over-current detector 88 or thermal switch 114, the power control processor 120 reduces the LF power by reducing the duty cycle of the LF power, and it transmits a signal to the user interface 122 to provide notification of the fault event. Persons skilled in the art are able to select appropriate circuitry to modify the duty cycle of the LF power consistent with the present invention.

Figure 5B:
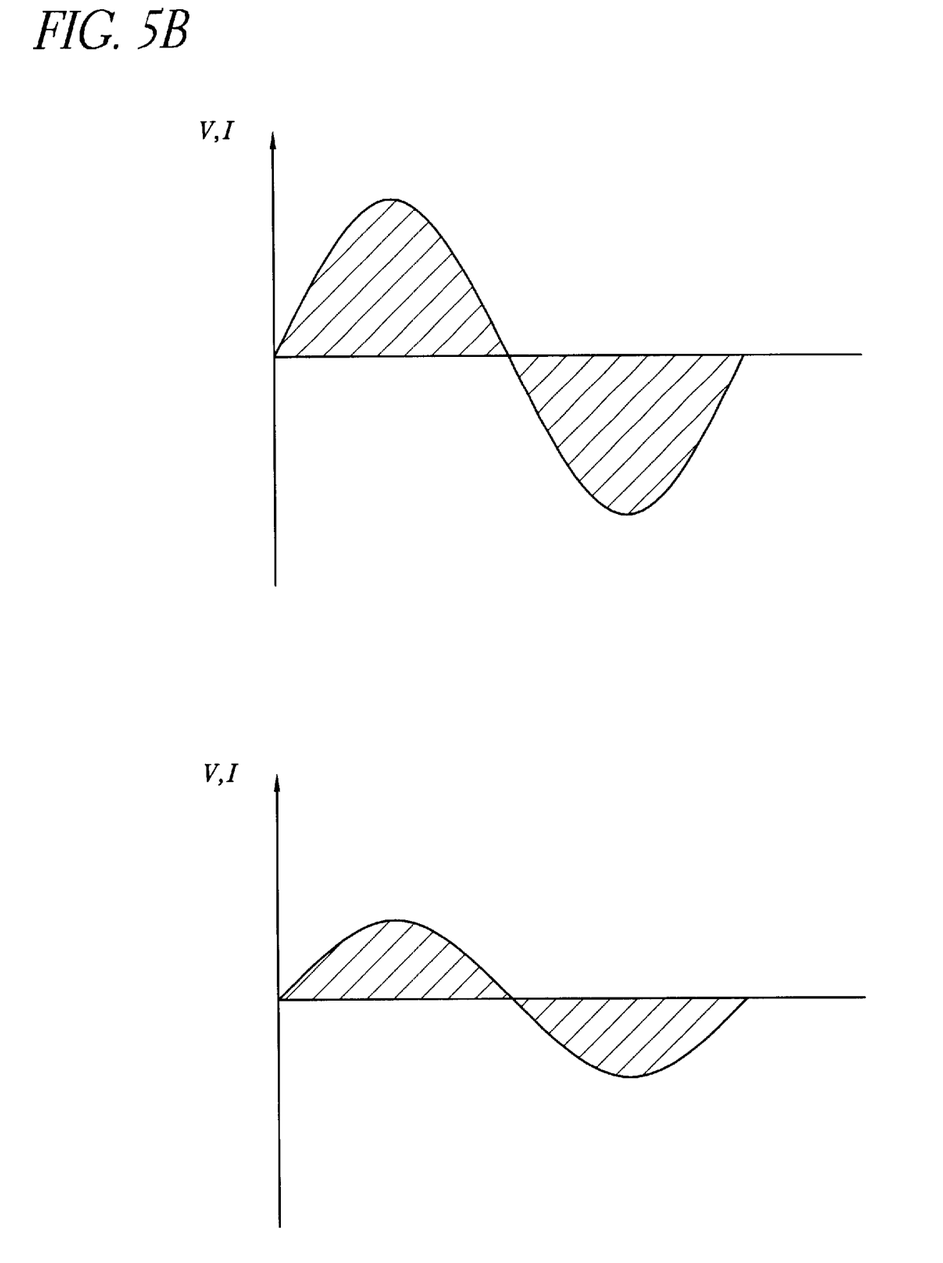
FIG. 5B schematically illustrates the amplitude control method of controlling the low frequency power applied to the plasma.

Alternatively, the LF power can be controlled by utilizing amplitude control, as in the embodiment illustrated in FIG. 4. Under amplitude control, the LF power is modified by adjusting the amplitude of the voltage and current applied between the electrode 32 and the vacuum chamber 12. FIG. 5B schematically illustrates the voltage and current corresponding to a first LF power setting and a second LF power setting less than the first LF power setting. During normal operations, the VCA 53 maintains a constant LF power applied to the plasma by actively adjusting the amplitude of the LF power in response to the feedback real-time signal received from the power control module 110 in response to the measured LF power. Persons skilled in the art are able to select appropriate circuitry to modify the amplitude of the LF power consistent with the present invention.

The electronics for RF sterilizers are complicated by the need of such systems to attempt to closely match the output impedance of the RF generator with the plasma impedance at all times in order to maximize power efficiency and to avoid damage to the RF generator. Plasma impedance varies widely during plasma formation, being very high until the plasma is fully formed, and very low thereafter. When first igniting a plasma, the RF generator cannot match the high plasma impedance which exists prior to the full formation of the plasma, so a large fraction of the power output is reflected back to the RF generator. RF generators have protection systems which typically limit the RF generator output during periods of high reflected power to avoid damage. However, to ignite the plasma, the voltage output of the RF generator must exceed the threshold voltage required for plasma ignition. The threshold voltage is dependent on the chamber pressure, reactive agent, and other operating parameters and is approximately 300 $V_{rms}$. In an RF system, once ignition has been achieved, and the plasma impedance is thereby reduced, the magnitude of the applied RF voltage must be reduced to a sustaining voltage, e.g., approximately 140 $V_{rms}$, to avoid excessive power delivery. Because the higher RF voltages required for plasma ignition produce excessively high reflected power before full plasma formation, RF generators require complicated safeguards to prevent damage during the plasma ignition stage.

Conversely, the complexity and rate of ignition failures are significantly reduced for LF sterilizers since the LF sterilizers may operate using applied voltages above the threshold voltage and have much less restrictive output impedance matching requirements. During the times at which the applied LF voltage equals zero, as seen in FIG. 5A, the LF plasma is extinguished and there is no LF plasma in the vacuum chamber. The LF plasma must then be re-ignited twice each cycle. By only operating in one voltage regime, LF sterilizers have simpler and more reliable electrical systems than do RF sterilizers. These electrical systems are easier to service and diagnose, thereby reducing the costs associated with repair. In addition, the higher peak plasma densities resulting from LF sterilizers likely result in increased dissociative recombination on the articles, thereby reducing the amount of residual reactive species remaining on the articles after the sterilization procedure.

Figure 6:
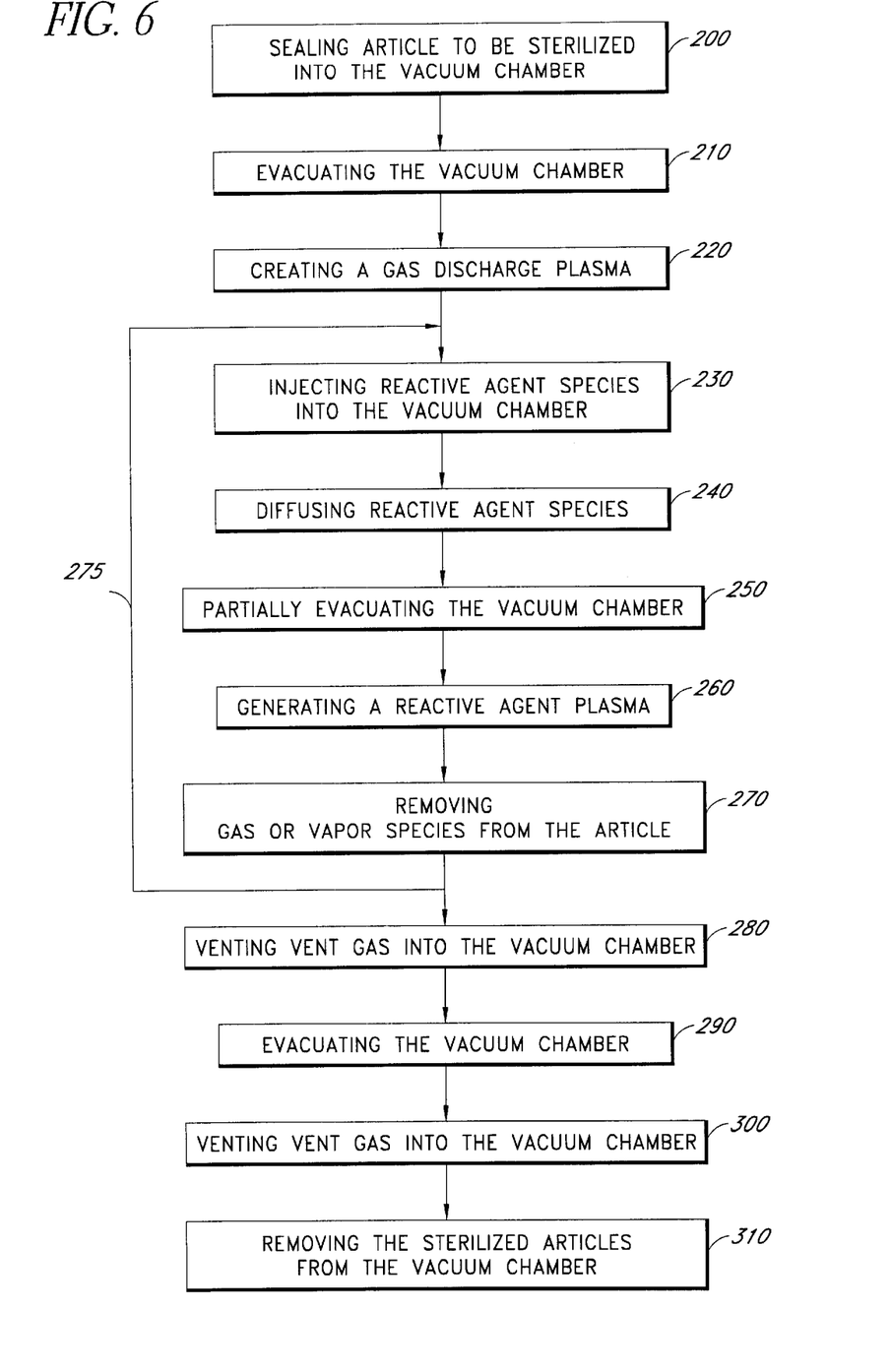
FIG. 6 schematically illustrates a preferred embodiment of a method of sterilization compatible with the present invention.

FIG. 6 schematically illustrates a preferred method of sterilization using the apparatus schematically illustrated in FIG. 1. The sterilization process shown in FIG. 6 is exemplary, and persons skilled in the art recognize that other processes are also compatible with the present invention. The preferred process begins by sealing 200 the article to be sterilized into the vacuum chamber 12. The vacuum chamber is then evacuated 210 by engaging the vacuum pump 14 and the vacuum valve 16 under the control of the process control module 30. The vacuum chamber 12 is preferably evacuated to a pressure of less than approximately 660 Pa (5 Torr), more preferably between approximately 25 to 270 Pa (0.2 to 2 Torr), and most preferably between approximately 40 to 200 Pa (0.3 to 1.5 Torr).

In an exemplary process, upon reaching a desired pressure in the vacuum chamber 12, the process control module 30 signals the LF power module 22 to energize the electrode 32 within the vacuum chamber 12. By applying a LF voltage to the electrode 32, the LF power module 22 ionizes the residual gases in the vacuum chamber 12, thereby creating 220 a gas discharge LF plasma inside the vacuum chamber 12. This gas discharge LF plasma is formed from the residual gases in the vacuum chamber 12, which are primarily air and water vapor. Because this gas discharge LF plasma is created 220 before the reactive agent is injected into the vacuum chamber 12, this gas discharge LF plasma is typically called the "pre-injection" plasma. The vacuum valve 14 is controllably opened and closed to maintain a preset vacuum pressure during the pre-injection plasma step 220. The pre-injection plasma heats the surfaces inside the vacuum chamber 12, including the articles, thereby aiding the evaporation and removal of condensed water and other absorbed gases from the vacuum chamber 12 and the articles. A similar pre-injection plasma is described by Spencer, et al. in U.S. Pat. Nos. 5,656,238 and 6,060,019, which are incorporated by reference herein. In an exemplary process, the pre-injection plasma is turned off after approximately 0 to 60 minutes. Other embodiments that are compatible with the present invention do not include the creation of the pre-injection plasma, or use multiple pre-injection plasmas. In still other embodiments, the vacuum chamber 12 can be vented after the articles are exposed to the pre-injection plasma.

In the preferred process, upon reaching a desired chamber pressure, the vacuum valve 16 is closed, and the reactive agent valve 20 is opened under the control of the process control module 30, thereby injecting 230 reactive agent from the reactive agent source 18 into the vacuum chamber 12 via the reactive agent line 19. In the preferred embodiment, the reactive agent comprises hydrogen peroxide, which is injected in the form of a liquid which is then vaporized. The injected liquid contains preferably from about 3% to 60% by weight of hydrogen peroxide, more preferably from about 20% to 60% by weight of hydrogen peroxide, and most preferably from about 40% to 60% by weight of hydrogen peroxide. The concentration of hydrogen peroxide vapor in the vacuum chamber 12 may range from 0.125 to 20 mg of hydrogen peroxide per liter of chamber volume. The higher concentrations of hydrogen peroxide will result in shorter sterilization times. Air or inert gas such as argon, helium, nitrogen, neon, or xenon may be added to the chamber with the hydrogen peroxide to maintain the pressure in the vacuum chamber 12 at the desired level. This injection 230 of reactive agent may occur as one or more separate injections.

Due to this injection 230 of reactive agent, the chamber pressure of the preferred process rises to approximately 2000 Pa (15 Torr) or more. After approximately 6 minutes into the injection stage 230, the reactive agent is permitted to diffuse 240 completely and evenly throughout the vacuum chamber 12. After approximately 1–45 minutes of diffusing 240, the reactive agent is substantially in equilibrium inside the vacuum chamber 12. This diffusing 240 allows the reactive species to diffuse through the packaging material of the articles, and come into close proximity, if not contact, with the surfaces of the articles, thereby sterilizing the articles. In other embodiments, the diffusion of the reactive agent can be immediately followed by a vent of the vacuum chamber 12.

The vacuum chamber 12 is then partially evacuated 250 by pumping out a fraction of the reactive agent from the vacuum chamber 12 by controllably opening the vacuum valve 16 under the control of the process control module 30. Once the vacuum pressure within the vacuum chamber 12 has reached the desired pressure, the vacuum valve 16 is controllably adjusted to maintain the desired pressure, and the process control module 30 signals the LF power module 22 to energize the electrode 32 within the vacuum chamber 12. In the preferred embodiment in which the reactive agent comprises hydrogen peroxide, the pressure of the hydrogen peroxide in the vacuum chamber 12 is preferably less than approximately 670 Pa (5 Torr), more preferably between approximately 25 and 270 Pa (0.2 to 2 Torr), and most preferably between approximately 40 and 200 Pa (0.3 to 1.5 Torr). By applying a LF voltage to the electrode 32, the LF power module 22 generates 260 a reactive agent LF plasma inside the vacuum chamber 12 by ionizing the reactive agent. The article is exposed to the reactive agent LF plasma for a controlled period of time. In the preferred embodiment, an additional cycle 275 is performed. Other embodiments may omit this additional cycle 275, or may include further cycles.

In both RF and LF plasmas, the components of the reactive agent plasma include dissociation species of the reactive agent and molecules of the reactive agent in excited electronic or vibrational states. For example, where the reactive agent comprises hydrogen peroxide as in the preferred embodiment, the reactive agent plasma likely includes charged particles such as electrons, ions, various free radicals (e.g., OH, $O_2H$), and neutral particles such as ground state $H_2O_2$ molecules and excited $H_2O_2$ molecules. Along with the ultraviolet radiation produced in the reactive agent plasma, these reactive agent species have the potential to kill spores and other microorganisms.

Once created, the charged particles of the reactive agent plasma are accelerated by the electric fields created in the vacuum chamber 12. Because of the fluid communication between the first region 31 and the second region 33, some fraction of the charged particles created in the first region 31 are accelerated to pass from the first region 31 to the second region 33 which contains the articles.

Charged particles passing from the first region 31 to the second region 33 have their trajectories and energies affected by the electric potential differential of the sheath regions between the plasma and the walls of the vacuum chamber 12 and the electrode 32. These sheath regions are created by all electron-ion plasmas in contact with material walls, due to charged particles impinging from the plasma onto the walls. Electrons, with their smaller mass and hence greater mobility, are lost from the plasma to the wall before the much heavier and less mobile ions, thereby creating an excessive negative charge density surrounding the walls and a corresponding voltage differential which equalizes the loss rates of the electrons and the ions. This voltage differential, or sheath voltage, accelerates electrons away from the wall surface, and accelerates positive ions toward the wall surface.

The sheath voltage varies for different plasma types, compositions, and methods of production. For RF plasmas, the sheath voltage is typically 40%–80% of the RF voltage applied to the electrode 32. For example, for a root-mean-squared (RMS) RF voltage of 140 $V_{rms}$ applied to the electrode 32 once the RF plasma is established, the corresponding sheath voltage is approximately 55–110 $V_{rms}$. An ion entering the sheath region surrounding the electrode 32 will then be accelerated to an energy of 55–110 eV. This acceleration of positive ions by the sheath voltage is the basic principle behind semiconductor processing by RF plasmas.

As described above, for the LF plasmas of the preferred embodiment of the present invention, the voltage applied to the electrode 32 may be equal to or greater than the ignition threshold voltage, which is typically 300 $V_{rms}$. In addition, for LF plasmas, the sheath voltage is typically a higher percentage of the applied voltage than for RF plasmas, so the sheath voltage of the preferred embodiment of the present invention is then much higher than the sheath voltage for an RF plasma system. This higher sheath voltage thereby accelerates the charged particles of the LF plasma to much higher energies. Therefore, because the charged particles are accelerated to higher energies, the charged particles of the LF plasma of the preferred embodiment travel farther and interact more with the articles than do the charged particles of RF plasma sterilizers.

Since the LF electric field changes polarity twice each cycle, the direction of the electric field acceleration on the charged particles reverses twice each cycle. For charged particles in the first region 31, this oscillation of the direction of the acceleration results in an oscillation of the position of the charged particles. However, because of the fluid communication between the first region 31 and the second region 33, some fraction of the charged particles are able to pass to the second region 33 containing the articles from the first region 31 before the direction of the electric field acceleration reverses.

The fraction of the charged particles created in the reactive agent LF plasma which enter the second region 33 is a function of the frequency of the applied electric field. The charged particles have two components to their motion—random thermal speed and drift motion due to the applied electric field. The thermal speed, measured by the temperature, is the larger of the two (typically approximately $10^7$–$10^8$ cm/sec for electrons), but it does not cause the charged particles to flow in any particular direction. Conversely, the drift speed is directed along the electric field, resulting in bulk flow of charged particles in the direction of the applied electric field. The magnitude of the drift speed is approximately proportional to the magnitude of the applied electric field, and inversely proportional to the mass of the charged particle. In addition, the magnitude of the drift speed is dependent on the gas species and chamber pressure. For example, for typical operating parameters of gas discharge plasma sterilizers, including an average electric field magnitude of approximately 1 volt/cm, the drift speed for an electron formed in a gas discharge plasma is typically approximately $10^6$ cm/sec.

A charged particle enters the second region 33 containing the articles only if it reaches the second region 33 before the polarity of the applied electric field changes, which would reverse the acceleration of the charged particle away from the electrode 32. For example, for an applied RF electric field with a frequency of 13.56 MHz, the period of the electric field is approximately $7.4 \times 10^{-8}$ sec, so an electron only moves a distance of approximately $3.7 \times 10^{-3}$ cm during the half-cycle or half-period before the direction of the electric field changes and the electron is accelerated away from the electrode 32. Due to their much larger masses, ions move much less than do electrons. Where the first region 31 between the vacuum chamber 12 and the electrode 32 is approximately 2.54 cm wide, as in the preferred embodiment, only a fraction of the charged particles created by an RF plasma would actually reach the second region 33 containing the articles.

Conversely, for an applied LF electric field with a frequency of 60 Hz, the period of the electric field is approximately $16.7 \times 10^{-3}$ sec, so an electron can move approximately $8.35 \times 10^3$ cm before it is accelerated away from the electrode 32. Therefore, the use of LF voltages to create the plasma in the sterilization system 10 of the preferred embodiment results in more activity in the second region 33, as compared to a plasma generated using RF voltages. This higher activity in LF sterilizers likely contributes to the increased efficiency for the removal of residual reactive species from the sterilized articles as compared to RF sterilizers.

The plasma decay time, defined as a characteristic time for the plasma to be neutralized after power is no longer applied, provides an approximate demarcation between the LF and RF regimes. The plasma decay time is not known precisely, but it is estimated to be approximately $10^{-4}$–$10^{-3}$ sec for the plasma densities used in sterilizer systems, such as the preferred embodiment of the present invention. This plasma decay time corresponds to the time a charged particle exists before it is neutralized by a collision with a surface or another plasma constituent, and is dependent on the plasma species generated and the geometries of the various components of the sterilization system 10. As described above, the LF regime is characterized by a plasma which is extinguished and re-ignited twice each cycle, i.e., the half-period of the applied LF voltage is greater than the plasma decay time. Therefore, the sterilization system 10 is continually run at an applied voltage above the ignition threshold voltage of the plasma in order to re-ignite the plasma. The estimated approximate range of plasma decay times of $10^{-4}$–$10^{-3}$ sec for many of the plasmas compatible with the present invention then translates to an upper limit on the low frequency regime of approximately 1–10 kHz. However, under certain circumstances, higher frequencies can be tolerated.

Alternatively, the upper limit of the low frequency regime may be defined as the frequency at which the electron drift speed is too slow for an electron to traverse the 2.54-cm-wide first region 31 during a half-period of the applied LF voltage. Under typical operating geometries, this upper limit of the low frequency regime would be approximately 200 kHz. For other geometries, the upper limit of the low frequency regime can be correspondingly different.

In the preferred embodiment of the present invention, the frequency of the LF voltage applied to the plasma is preferably from 0 to approximately 200 kHz, more preferably from 0 to approximately 10 kHz, still more preferably from 0 to approximately 1 kHz, and even more preferably from 0 to approximately 400 Hz. When selecting the frequency of the LF voltage applied to the plasma, the frequency is most preferably selected to have a half-period greater than the plasma decay time of the plasma.

In the preferred method, the LF power module 22 remains energized for approximately 2–15 minutes, during which the plasma removes excess residual reactive species present on surfaces within the vacuum chamber 12, including on the articles. There is a brief rise of the vacuum pressure upon generating 260 the plasma, however, the majority of the residual removal step 270 is conducted at an approximately constant vacuum pressure of 50 to 70 Pa (0.4 to 0.5 Torr). The residual removal step 270 is ended by the process control module 30, which turns off the LF power module 22, thereby quenching the plasma.

After the residual removal step 270, the vacuum chamber 12 is vented 280 by the process control module 30 which opens the vent valve 28, thereby letting in vent gas from the vent 26 through the vent line 27 and the vent valve 28. In the preferred process, the vacuum chamber 12 is then evacuated 290 to a pressure of approximately 40 to 105 Pa (0.3 to 0.8 Torr) to remove any remaining reactive agent which may be present in the vacuum chamber 12. The vacuum chamber 12 is then vented again 300 to atmospheric pressure, and the sterilized articles are then removed 310 from the vacuum chamber 12.

The LF plasma provides a reduction of the amount of residual reactive agent molecules remaining on the articles after the sterilization procedure is complete. Where the reactive agent comprises hydrogen peroxide, the amount of residual hydrogen peroxide remaining on the sterilized articles is preferably less than approximately 8000 ppm, more preferably less than approximately 5000 ppm, and most preferably less than approximately 3000 ppm. In a comparison of the amount of residual hydrogen peroxide remaining after a LF plasma sterilization as compared to a RF plasma sterilization, nine polyurethane test samples were exposed to hydrogen peroxide during a simulated sterilization cycle in both a LF sterilizer and a RF sterilizer. Each sample was prepared by washing with Manuklenz® and drying prior to sterilization to avoid any cross contamination. The nine samples were then distributed uniformly across the top shelf of a standard industrial rack.

A full LF sterilization cycle, which matched nearly exactly the conditions of a standard RF sterilizer cycle, was used to perform the comparison. The full LF sterilization cycle included a 20-minute exposure to a pre-injection plasma, a first 6-minute hydrogen peroxide injection, a vent to atmosphere, a 2-minute diffusion, a first 2-minute post-injection plasma, a second 6-minute hydrogen peroxide injection, a vent to atmosphere, a 2-minute diffusion, a second 2-minute post-injection plasma, and a vent to atmosphere. Two fill LF sterilization cycles were performed and compared to two full RF sterilization cycles. As seen in Table 1, all parameters other than the post-injection plasma power were maintained as constant as possible from run to run.

TABLE 1

|  | LF Run 1 | LF Run 2 | RF Run 1 | RF Run 2 |
| --- | --- | --- | --- | --- |
| Pre-injection plasma power | 727 W | 779 W | 751 W | 752 W |
| First post-injection plasma power | 783 W | 874 W | 757 W | 756 W |
| Second post-injection plasma power | 755 W | 893 W | 758 W | 758 W |
| Chamber temp. | 45° C. nom. | 45° C. nom. | 45° C. nom. | 45° C. nom. |
| Injection system temp. | 65–75° C. | 65–75° C. | 65–75° C. | 65–75° C. |
| $H_2O_2$ concentration | 17 mg/l | 17 mg/l | 17 mg/l | 17 mg/l |
| Chamber pressure during plasma | 50 Pa (0.4 Torr) | 50 Pa (0.4 Torr) | 50 Pa (0.4 Torr) | 50 Pa (0.4 Torr) |

Variations in the pre-plasma power were ±3.5%, so the sample temperature was approximately constant from run to run. The samples were then removed and the residual analysis was performed.

The LF sterilizer used to generate the LF plasma was operated at 60 Hz, and with an inductor of 500 mH and a capacitor of 13.6 μF. LF plasma power was determined by multiplying the voltage across the LF plasma by the current, then averaging on an oscilloscope. The fluctuation level of the LF power was approximately 10%. Table 2 illustrates the results of the comparison.

TABLE 2

|  | LF Run 1 | LF Run 2 | RF Run 1 | RF Run 2 |
| --- | --- | --- | --- | --- |
| Average post-injection plasma power | 769 W | 884 W | 757 W | 757 W |
| $H_2O_2$ residuals (ppm) | 1973 ± 144 | 1864 ± 75 | 2682 ± 317 | 2510 ± 203 |

Exposure to a LF post-injection plasma reduced the residual reactive species more effectively than did exposure to a RF post-injection plasma of comparable power. LF Run 1 had approximately 23% less residual hydrogen peroxide than either RF Run 1 or RF Run 2, even though all had approximately the same post-injection plasma power. The LF processes therefore resulted in less residual hydrogen peroxide than did the corresponding RF process.

The comparison of the two LF sterilization cycles illustrates that increased plasma power results in a reduction of the hydrogen peroxide residuals. Furthermore, the variation between samples, as indicated by the standard deviation of the residual measurements, was significantly reduced in the LF process, thereby indicating an increased uniformity as compared to the RF process.

Although described above in connection with particular embodiments of the present invention, it should be understood the descriptions of the embodiments are illustrative of the invention and are not intended to be limiting. Various modifications and applications may occur to those skilled in the art without departing from the true spirit and scope of the invention as defined in the appended claims.

What is claimed is:

1. A method of sterilization of an article, the method comprising:
   placing the article in a first region of a vacuum chamber;
   evacuating the vacuum chamber to a predetermined pressure;
   introducing gas or vapor species into the vacuum chamber;
   generating a plasma within the vacuum chamber by applying an applied electric field in a second region of the vacuum chamber, the second region in fluid communication with the first region, the first region having an electric field weaker than the applied electric field in the second region, the applied electric field having a frequency of less than 10 kHz; and
   maintaining the plasma for a time period sufficient to substantially remove gas or vapor species from the article.

2. The method as defined in claim 1, wherein the gas or vapor species comprises hydrogen peroxide.

3. The method as defined in claim 2, wherein the concentration of the hydrogen peroxide is at least 0.125 mg/liter.

4. The method as defined in claim 2, wherein an amount of hydrogen peroxide remaining on the article after maintaining the plasma is less than approximately 8000 ppm.

5. The method as defined in claim 1, wherein the applied electric field is applied in the second region by applying a voltage between two electrodes.

6. The method as defined in claim 5, wherein the voltage has a frequency from 0 to approximately 400 Hz.

7. The method as defined in claim 4, wherein the plasma has a plasma decay time and the voltage has a half-period greater than said plasma decay time.

8. The method as defined in claim 5, wherein the voltage has a frequency from 0 to approximately 1 kHz.

9. The method as defined in claim 5, wherein the vacuum chamber comprises one of the electrodes.

10. A method of sterilization of an article, the method comprising:
    placing the article in a first region of a vacuum chamber;
    evacuating the vacuum chamber to a predetermined pressure;
    generating a plasma within the vacuum chamber by applying an applied electric field in a second region of the vacuum chamber, the second region in fluid communication with the first region, the first region having an electric field weaker than the applied electric field in the second region, the applied electric field having a frequency of less than 10 kHz; and
    maintaining the plasma for a time period sufficient to heat the article to aid the evaporation and removal of water and other absorbed gases from the vacuum chamber and the article.

11. The method as defined in claim 10, wherein the applied electric field is applied in the second region by applying a voltage between two electrodes.

12. The method as defined in claim 11, wherein the voltage has a frequency from 0 to approximately 400 Hz.

13. The method as defined in claim 11, wherein the plasma has a plasma decay time and the voltage has a half-period greater than said plasma decay time.

14. The method as defined in claim 11, wherein the voltage has a frequency from 0 to approximately 1 kHz.

15. The method as defined in claim 11, wherein the vacuum chamber comprises one of the electrodes.

16. A system for sterilizing an article, the system comprising:

a first electrode;

a vacuum chamber coupled to a vacuum pump and a vent, wherein the vacuum chamber comprises a second electrode;

a first region within the vacuum chamber, the first region comprising a region between the first and second electrodes;

a second region within the vacuum chamber, the second region being in fluid communication with the first region, the second region adapted to receive the article;

a source of fluid coupled to the vacuum chamber;

a process control module; and a power module comprising components adapted to apply a voltage between the first electrode and second electrode so as to generate a plasma in the first region within the vacuum chamber, the voltage having a frequency of less than 10 kHz.

17. The system as described in claim 16, wherein the source of fluid comprises reactive agent species.

18. The system as described in claim 17, wherein the reactive agent species comprises a germicide.

19. The system as described in claim 18, wherein the germicide comprises hydrogen peroxide.

20. The system as described in claim 16, wherein the power module comprises a power controller, a flyback current shunt element, a current monitor, a voltage monitor, an inductor, a capacitor, and a power control module.

21. The system as described in claim 20, wherein the power control module is coupled to the process control module and the power controller, and the power controller is adapted to adjust the duty cycle of the voltage applied between the first and second electrodes in response to the power control module.

22. The system as described in claim 20, wherein the power control module is coupled to the process control module and the power controller, and the power controller is adapted to adjust the amplitude of the voltage applied between the first and second electrodes in response to the power control module.

23. The system as described in claim 20, wherein the power controller is adapted to maintain a substantially stable average power applied to the plasma.

24. The system as described in claim 20, wherein the inductor and capacitor comprises an LC circuit connected in series with the power controller.

25. The system as described in claim 24, wherein an inductance and a capacitance of the LC circuit are chosen to match a resonant frequency of the LC circuit to the frequency of the voltage applied between the first and second electrodes.

26. The system as described in claim 20, wherein the power module further comprises a switching module that in response to an input voltage provides an output voltage with a frequency different from the frequency of the input voltage.

27. The system as described in claim 16, wherein the applied voltage is from approximately 100 $V_{rms}$ to approximately 1000 $V_{rms}$.

28. The system as described in claim 16, wherein the applied voltage is from approximately 200 $V_{rms}$ to approximately 500 $V_{rms}$.

29. The system as described in claim 16, wherein the applied voltage is from approximately 250 $V_{rms}$ to approximately 450 $V_{rms}$.

30. The system as described in claim 16, wherein the voltage is above a threshold voltage required to ignite a plasma.

31. The system as described in claim 16, wherein the voltage has a frequency from 0 to approximately 400 Hz.

32. The system as defined in claim 16, wherein the plasma has a plasma decay time and the voltage has a half-period greater than said plasma decay time.

33. The system as described in claim 16, wherein the voltage has a frequency from 0 approximately 1 kHz.

* * * * *